US007929660B2

(12) United States Patent
Ullberg et al.

(10) Patent No.: US 7,929,660 B2
(45) Date of Patent: Apr. 19, 2011

(54) SUPPORT STRUCTURE FOR MAMMOGRAPHY

(75) Inventors: Christer Ullberg, Sollentuna (SE); Tomas Kristoffersson, Täby (SE)

(73) Assignee: XCounter AB, Danderyd (SE)

( * ) Notice: Subject to any disclaimer, the term of this patent is extended or adjusted under 35 U.S.C. 154(b) by 215 days.

(21) Appl. No.: 12/230,712

(22) Filed: Sep. 3, 2008

(65) Prior Publication Data

US 2010/0014634 A1    Jan. 21, 2010

(30) Foreign Application Priority Data

Jul. 18, 2008   (SE) ...................................... 0801710

(51) Int. Cl.
*A61B 6/04* (2006.01)
(52) U.S. Cl. .......................................... 378/37; 378/208
(58) Field of Classification Search ................... 378/37, 378/208
See application file for complete search history.

(56) References Cited

U.S. PATENT DOCUMENTS

| 7,327,825 | B2 | 2/2008 | Roncaglioni et al. | |
| 2004/0111801 | A1 | 6/2004 | Marin et al. | |
| 2006/0115041 | A1* | 6/2006 | Roncaglioni et al. | 378/37 |
| 2006/0210021 | A1* | 9/2006 | Matsumoto et al. | 378/196 |
| 2006/0262898 | A1 | 11/2006 | Partain et al. | |
| 2007/0076844 | A1 | 4/2007 | Defreitas et al. | |
| 2007/0133738 | A1 | 6/2007 | Zimmermann | |

FOREIGN PATENT DOCUMENTS

FR       2 882 246       8/2006

OTHER PUBLICATIONS

International-Type Search Report dated Dec. 22, 2008 for corresponding Swedish Application No. IDS/SE08/00311.

* cited by examiner

*Primary Examiner* — Hoon Song
*Assistant Examiner* — Mona M Sanei
(74) *Attorney, Agent, or Firm* — Harness, Dickey & Pierce, P.L.C.

(57) ABSTRACT

The invention relates to a support structure 1 for mammography, comprising a stand 2 and an arm structure 3 attached thereto. The support structure 1 further comprises a scanner head cover 6 attached to the arm structure 3. The scanner head cover 6 comprises a vertical side portion 6a, and is designed so that a cavity 12 is formed between the vertical surface portion 6a and a vertical part 3b of the arm structure 3, whereby the cavity 12 provides space for an arm of a patient during imaging. A more comfortable posture is provided for a patient.

16 Claims, 9 Drawing Sheets

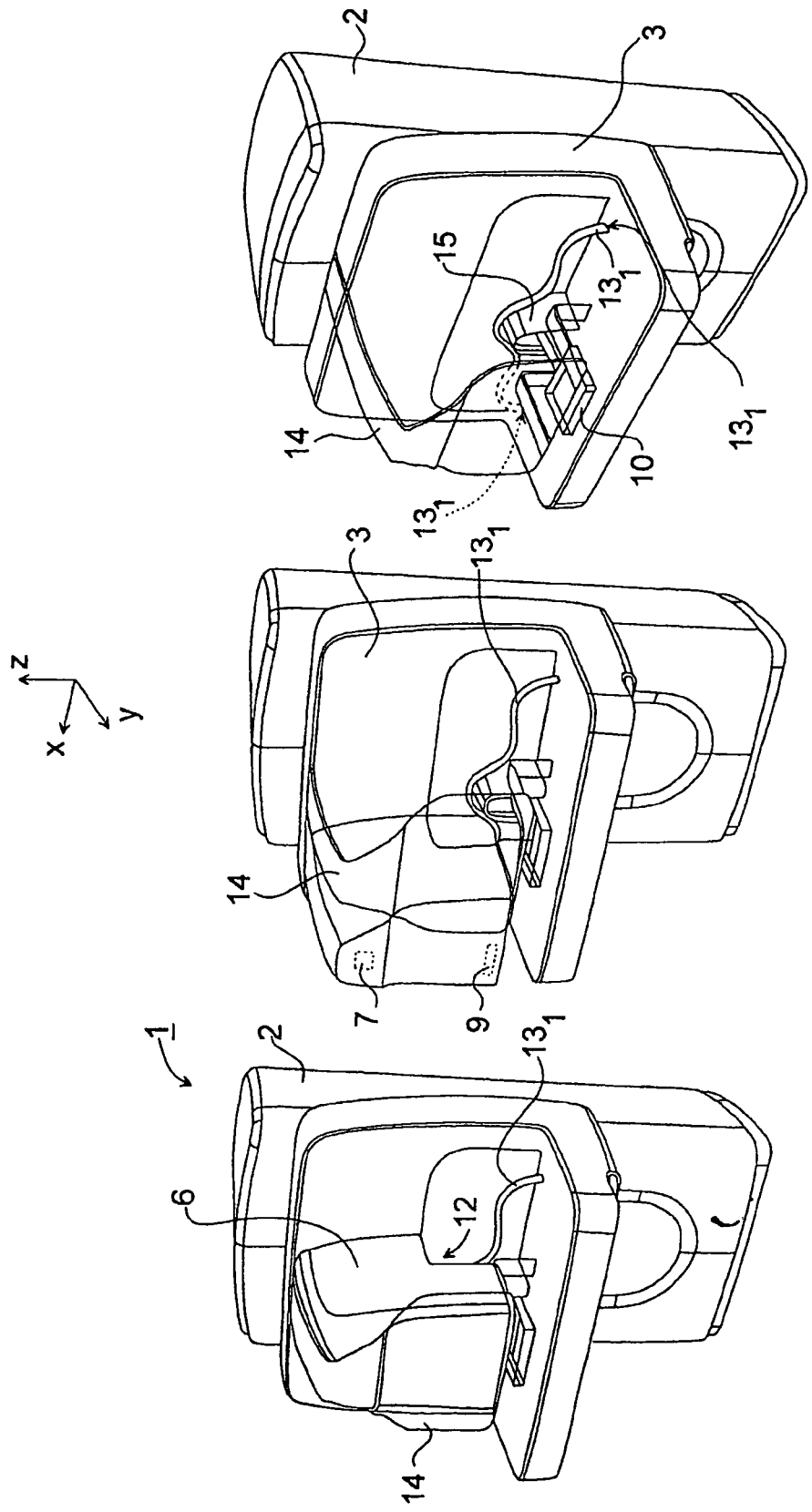

SUPPORT STRUCTURE FOR MAMMOGRAPHY

PRIORITY STATEMENT

The present application hereby claims priority under 35 U.S.C. §119 on Swedish patent application number 0801710-5 filed Jul. 18, 2008, the entire contents of which is hereby incorporated herein by reference.

FIELD OF THE INVENTION

The present invention is related to the field of mammography, and in particular to support structures for mammography.

BACKGROUND OF THE INVENTION

Mammography is an important application of medical imaging. In a mammography procedure of today the patient is standing up and her breast is put between two compression plates, which compresses the breast that is being imaged. An X-ray source is activated and an X-ray detector captures a 2D image of the breast. The compression of the breast is most uncomfortable to the patient.

Further, it is important that the image quality is high, since breast cancer can, for example, be missed by being obscured by radiographically dense, fibrograndular breast tissue. For example, it is important that the patient does not move during the imaging procedure since movements could adversely affect the image quality.

SUMMARY OF THE INVENTION

It can be difficult for the patient to stand still when her breast is being compressed and hurting; she may unintentionally move. Further, the position in which she is standing affects her ability to stand still. Today, the patient is often requested hold on to a handle arranged on a surface of the X-ray imaging apparatus. This is a rather uncomfortable position, requiring some balancing and the patient is again prone to move around and shift position in order to try to find a more comfortable position.

There are thus some drawbacks related to the field of mammography and it would be desirable to provide means for lessening the discomfort for the patient undergoing a mammography examination.

It is an object of the present invention to provide a support structure for mammography having an improved design, in order to thereby overcome or at least alleviate the above-mentioned drawbacks of the prior art.

It is another object of the invention to provide a support structure for mammography whereby a patient is provided a comfortable position during the imaging of her breasts.

It is yet another object of the invention to provide a support structure for mammography, whereby the radiation dose that a patient is exposed to is minimized.

It is still another object of the invention to provide a support structure for mammography, whereby the image quality of is not degraded by movements of the patient.

These objects, among others, are achieved by support structures for mammography as defined in the appended patent claims.

In accordance with the present invention, a support structure for mammography is provided. The invention relates to a support structure for mammography, comprising a stand and an arm structure attached thereto. The support structure further comprises a scanner head cover attached to the arm structure. The scanner head cover comprises a vertical side portion, and is designed so that a cavity is formed between the vertical surface portion and a vertical part of the arm structure, whereby the cavity provides space for an arm of a patient during imaging. By means of the invention, the patient experiences less discomfort during the examination compared to the prior art examinations. The patient can stand up in a relaxed yet steady position, and there is a lessened risk of the patient moving during the imaging. The quality of the images taken is thus not affected by movements of the patient. As one arm is put within the support structure and held steady therein, she is able to lean against the support structure in a relaxed manner, without having to balance with one arm on her back, or with the arm along the housing of the support structure as is standard procedure today. Further, the support structure provides a reliable way of performing the imaging without the patient unintentionally moving, thereby providing images of high quality. This also entails fewer re-examinations due to poor image quality, whereby the patient is subjected to fewer radiation occasions.

Further embodiments of the invention are defined in the dependent claims, the advantages of which should become clear when reading the detailed description.

Yet further characteristics of the invention and advantages thereof will be evident from the detailed description of embodiments of the present invention given hereinafter and the accompanying figures, which are only given by way of illustration, and thus are not limitative of the present invention.

BRIEF DESCRIPTION OF THE DRAWINGS

FIGS. 2*a*-2*c* illustrate an embodiment of an arm support device in accordance with the invention.

DETAILED DESCRIPTION OF EMBODIMENTS

Figure 1A:
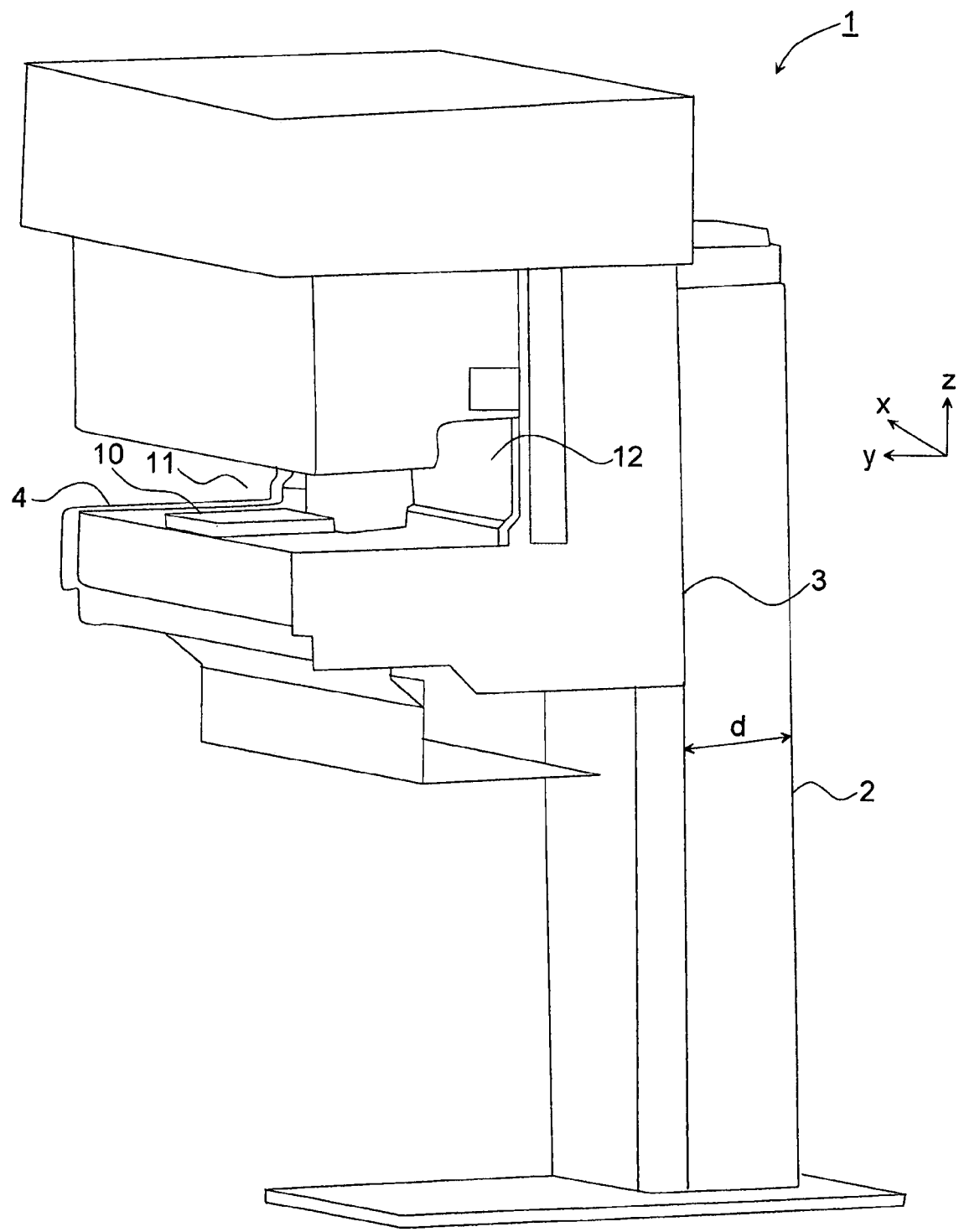
FIGS. 1*a*-1*c* illustrate in different views a support structure for mammography in accordance the invention.

Same reference numerals are used throughout the figures for denoting same or corresponding parts.

Figure 1B:
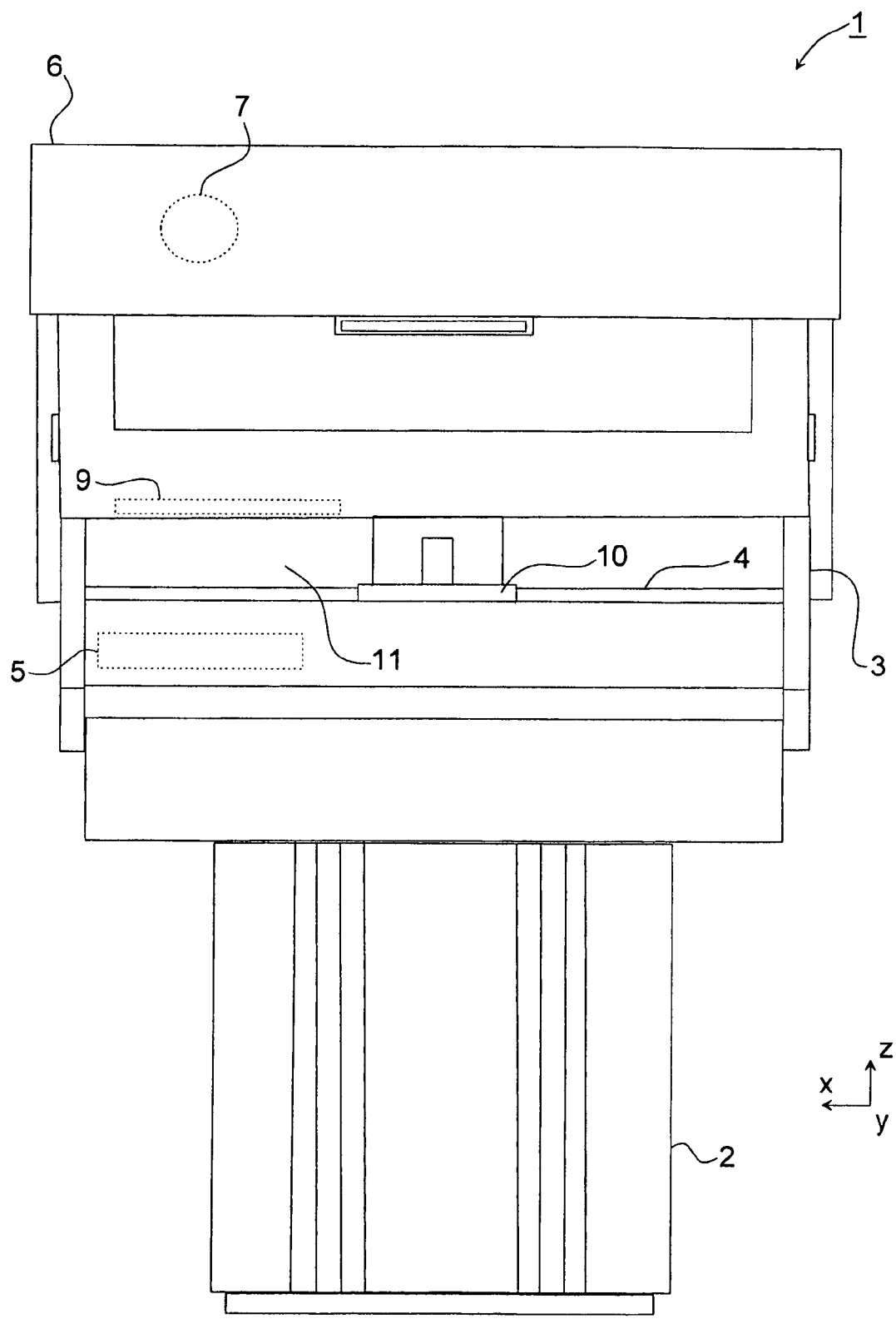
Figure 1C:
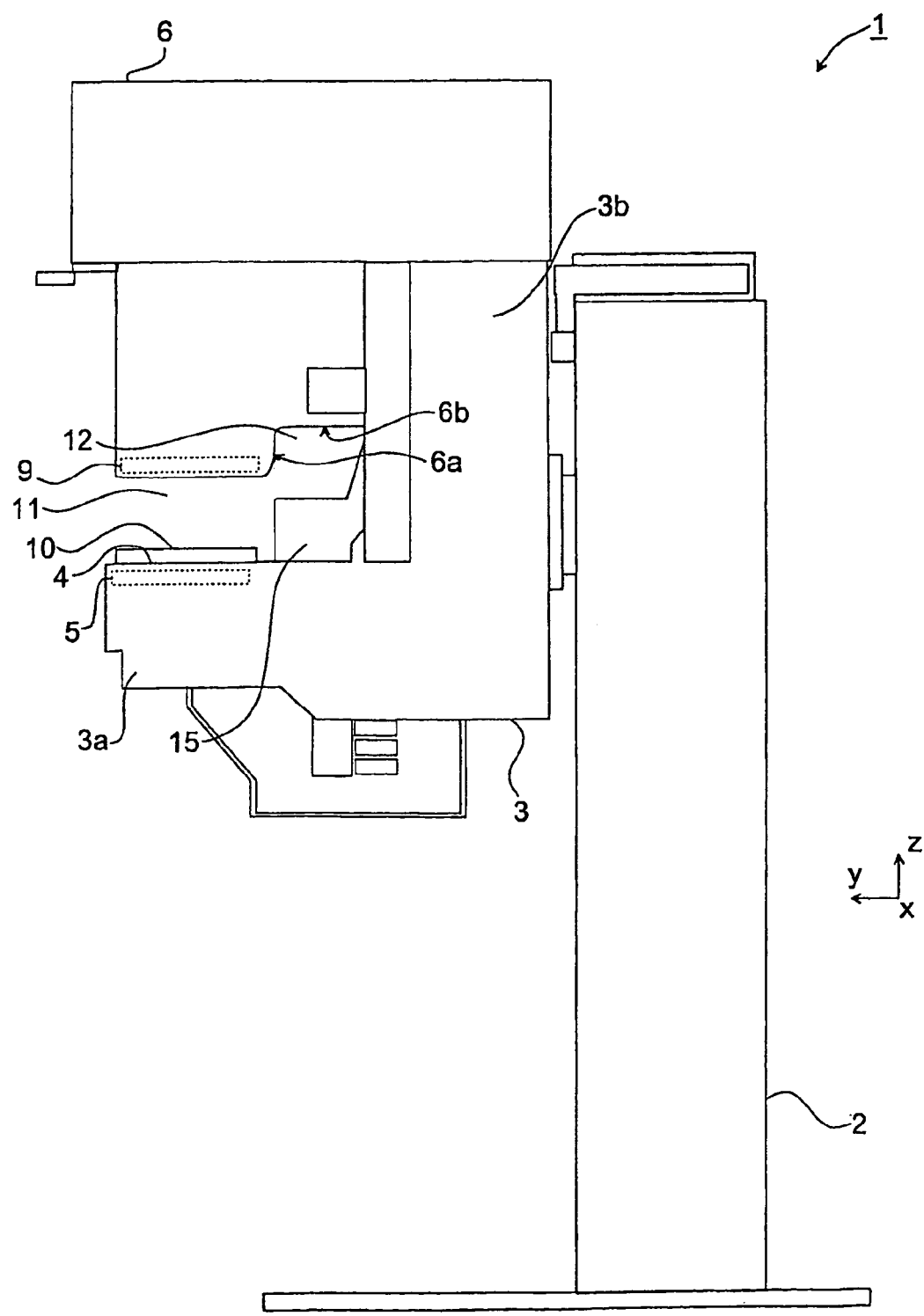

FIGS. 1*a*-1*c* illustrate a support structure for mammography in accordance with the invention. The support structure 1 comprises a stand 2 and an arm structure 3. The arm structure 3 is, for example, L-shaped, U-shaped or comprises an E-arm structure, and is attached to the stand 2 in a way so that it can be raised and lowered for providing a most comfortable position for a patient irrespective of her length. Further, the arm structure 3 can be rotated in a z-x-plane, wherein the z-axis is a vertical axis parallel to the height direction of the stand 2, the x-axis is a horizontal axis parallel to the width of the stand 2 (i.e. parallel to the side of the stand 2 to which the arm structure 3 is attached) and the y-axis is the axis parallel to the depth of the stand 2 (the depth being denoted by d in the FIG. 1a).

When the right breast of a patient is to be imaged, the arm structure 3 is tilted to the left (in the z-x-plane). The arm structure 3 may be tilted any suitable angle between 0 and 180 degrees, for example in the range of 45-60 degrees; an angle of about 60 degrees provides a comfortable position for the patient. Similarly, when the left breast of the patient is to be imaged, the arm structure 3 is tilted to the right (in the z-x-plane).

The arm structure 3 comprises at least a horizontal lower part 3a and a vertical part 3b (see FIG. 1c). The lower part 3a of the arm structure 3 comprises an object table 4 onto which the patient places her breast. The lower part 3a further comprises an X-ray detector 5, only schematically illustrated in the figure, which X-ray detector 5 is moved in the x-y-plane. The X-ray detector 5 can thus make a scanning movement in the x-y-plane. However, in other embodiments of the invention, the X-ray detector 5 may be scanned in other directions as well, for example along a curve, performing an arched scanning along an arched trajectory.

A scanner head cover 6 is attached to the arm structure 3 at a suitable location above the object table 4. In the embodiment illustrated in FIGS. 1a-1c, the width of the scanner head cover (width defined as being along x-axis) is essentially equal to the width of the object table 4. The X-ray source 7 and the detector device 5 are in this embodiment arranged to be moved with the scanner head cover 6. However, in alternative embodiments (illustrated in the following figures), the scanner head cover 6 may be fastened to the arm structure 3 so as to be movable in the z-x-plane. That is, the scanner head cover 6 can be scanned over a breast when the breast is placed on the object table 4.

The scanner head cover 6 can further be rotated in the z-x-plane, i.e. around the y-axis. As the arm structure 3 is rotated in the z-x-plane, the scanner head cover 6 is also rotated. The scanner head cover 6 could also be rotatable in relation to the arm structure 3 to which it is attached.

If the scanner head cover 6 is moved in relation to the object table 4 during scanning, i.e. has a smaller width than the object table, there is an additional advantage in that a physician preparing the patient for an examination can easily position the breast on the object table 4 without being hindered by the scanner head cover 6. In particular, as the scanner head cover 6 is tilted when the arm structure 3 is tilted (rotated), there is space for such positioning by the physician. This also enables the physician to optimize the placement of the breast, and thereby minimize the risk of having to repeat the procedure by taking images that are not good enough for evaluation.

An X-ray source 7, schematically indicated in the figure, is arranged within the scanner head cover 6. The X-ray source 7 can be any X-ray source suitable for use in a mammography application. In an alternative embodiment, instead of scanning the scanner head cover 6 over the breast, the X-ray source 7 is arranged to be moved within the scanner head cover 6, while the scanner head cover 6 is kept still.

The movements of the X-ray detector 5 and the X-ray source 7 are synchronized, so that X-rays transmitted from the X-ray source 7 are transmitted through the breast of a patient and received by the X-ray detector 5.

A collimator 9 may be arranged between the scanner head cover 6 and the object table 4. The collimator 9 is, for example, arranged within the scanner head cover 6 in any suitable manner, located below the X-ray source 7, both of which moves when the scanner head cover 6 is moved along the x-axis during a scanning. The collimator is arranged to filter a stream of X-rays from the X-ray source 7 so that only those traveling parallel to a specified direction are allowed through, all in conventional manner. It is noted that a collimator is not necessary for all types of detector devices, and is thus used or omitted in dependence on type of detector device.

A compression plate 10 is further provided. The compression plate 10 is attached to a protruding part 15 of the arm structure 3. The attachment is such that the compression plate 10 can be raised and lowered. In particular, the compression plate 10 is raised or moved upward (in the z-direction) so that a breast can be placed on the object table 4, whereupon it is lowered and pressed against the breast during the imaging. The compression plate 10 is thus pressed against the breast placed on the object table 4 in a known manner. However, in accordance with the invention, the pressure on the breast can be decreased owing to the improved detector device 5 as well as owing to the improved support structure 1 allowing a more comfortable posture of the patient. The examination is thereby less trying for the patient compared to the state of the art.

In accordance with the invention, the arm, or parts thereof, of the patient should be put in a cavity formed behind the scanner head cover 6, i.e. in a cavity formed between the scanner head cover 6 and the arm structure 3. To this end, the scanner head cover 6 and/or the arm structure 3 are/is designed so that a cavity is formed for providing space in which the patient places her arm. Such cavity, or open space, is indicated in FIGS. 1a and 1c at reference numeral 12. More specifically, the scanner head cover 6 comprises a vertical surface portion 6a (FIG. 1c) facing the vertical part 3b of the arm structure 3. The cavity 12 is thus formed between the vertical surface portion 6a and a surface portion of the vertical part 3b of the arm structure 3. Two surfaces of the scanner head cover 6 and one surface of the arm device 3 surround the cavity 12. The two surfaces of the scanner head cover 6 are the mentioned vertical surface portion 6a and a horizontal surface portion 6b that is perpendicular to the vertical surface portion 6a and perpendicular to the vertical part 3b of the arm structure 3. It is noted that the vertical surface portions mentioned above are essentially vertical, but could be somewhat angled.

In another embodiment the scanner head cover 6 and/or the arm structure 3 is/are designed so that a cavity 12 is formed between them. For example, the cavity could be formed between the surface portion 6a and an opposing surface part 3b of the arm structure 3, and such cavity 12 providing the space for an arm of a patient during imaging.

The upper part of the arm is kept on the object table 4, but well away from a radiation area or imaging area 11, and the cavity 12 provides space for the lower part of the arm (forearm). The arm should be kept away from the X-rays occurring in the imaging area 11 during the whole examination while the X-ray source 7 is moved over the breast. This is in contrast with known mammography arrangements, wherein the arm is kept away from the object table 4 entirely.

The cavity 12 may be provided by designing the scanner head cover 6 in a suitable manner. For example, the scanner head cover 6 may have a stepped shape, i.e. it may be designed to have a recess on the part closest to the arm structure 3. Stated differently, the side of the scanner head cover 6 being attached to the arm structure 3 has a smaller height (height being measured along the z-axis) than the opposite side, i.e. the side facing the patient.

The cavity 12 may thus be a simple recess mentioned above, wherein the cavity comprises a horizontal rectangular hole. The cavity 12 may alternatively comprise a tubular hole or tubular indent provided in the arm structure 3, into which the arm is inserted. Such tubular hole, having an opening essentially perpendicular to the object table 4, can be angled, i.e. the centre axis of the tubular hole makes an angle with the z-axis. Such angle could range from anywhere between zero and 90°, chosen so as to be comfortable when inserting the arm therein.

An arm support device, described next, is provided to keep the arm at the desired location, away from the X-rays.

FIGS. 2a-2c illustrate a first exemplary arm support device $13_1$, wherein the scanner head cover 6 is removed altogether in FIG. 2c in order to illustrate the arm support device $13_1$ more clearly. The arm support device $13_1$ can be a handle bar arrangement as illustrated in the figure. The shape of the arm support device $13_1$ can be chosen so as to maximise the support function and to make the posture of the patient during imaging as comfortable as possible. The arm structure 3 may comprise a protruding part 15 for holding the compression plate 10 in an upwards and downwards movable way, as described earlier. The arm support device $13_1$ is then suitably designed so that it is arranged above the protruding part 15. The arm support device $13_1$ may for example comprise a bar, ledge, rim or list having a semicircular shape, or comprising bends as illustrated in the FIGS. 2a-2c. The arm support device $13_1$ is preferably symmetrical so as to display the same shape and function when imaging the right and left breast, i.e. when putting in the right or left arm into the cavity 12 behind the scanner head cover 6. During imaging, the forearm of a patient rests against the support device $13_1$ while the upper arm rests against the object table 4. The patient may also grab hold of the arm support device $13_1$ for additional support. One such arm support device $13_1$ is placed on both sides of the imaging area as seen in the x-direction.

FIGS. 2a-2c further illustrate another feature of the present invention. The support structure for mammography 2 may comprise a shield 14 that wraps around the scanner head cover 6. The shield 14 is attached to the arm structure 3 so as to be located in front of (as seen in the negative y-direction) the imaging area 11, thereby preventing the patient and her arm from being hit by the scanner head cover 6 during imaging.

Figure 3C:
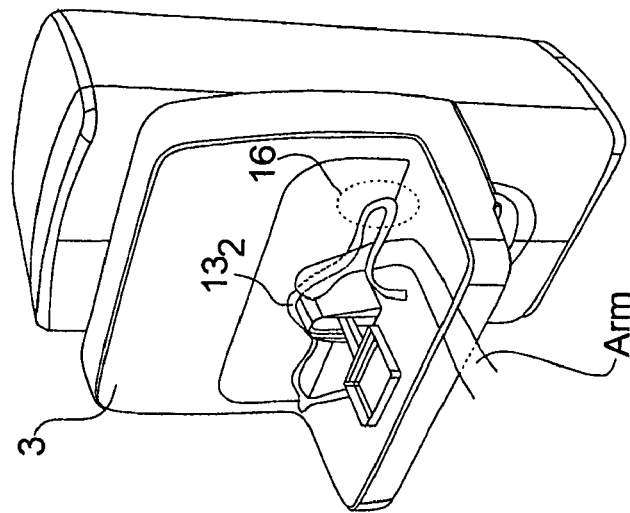
FIGS. 3*a*-3*c* illustrate another embodiment of an arm support device in accordance with the invention.
Figure 3B:
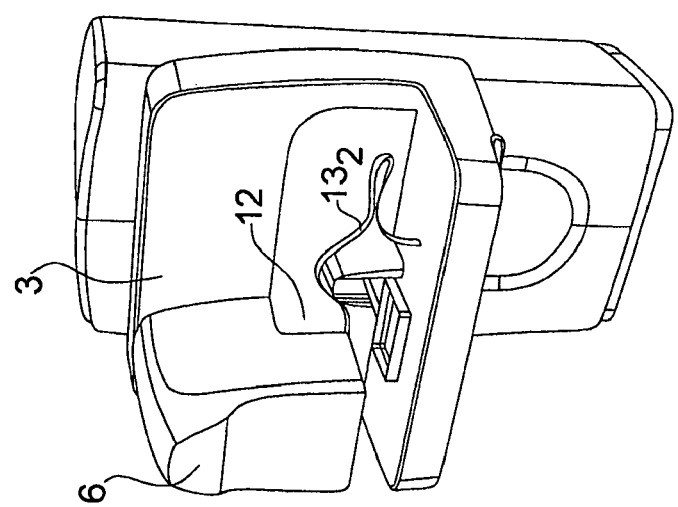
Figure 3A:
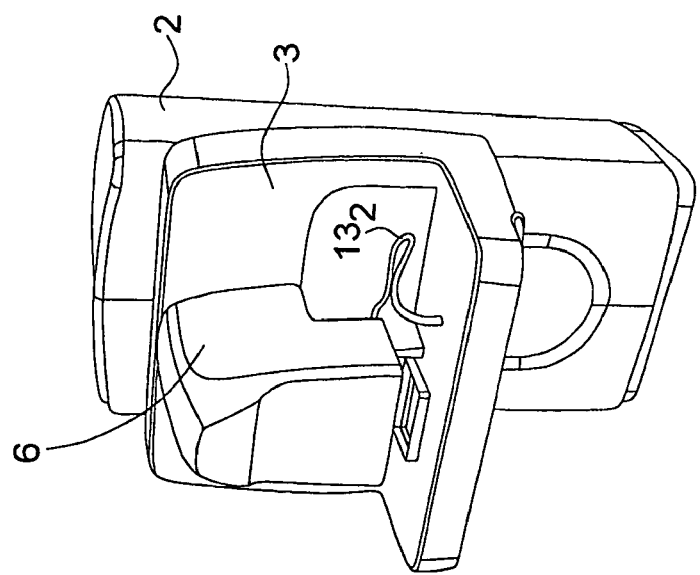

FIGS. 3a-3c illustrate another embodiment of the arm support device. The scanner head cover 6 is moved in relation to the arm structure 3, to which it is attached, along the x-axis as is illustrated in FIGS. 3a and 3b, wherein the scanner head cover 6 has moved a small distance. In FIG. 3c the scanner head cover 6 has been removed for clarity. The arm support device $13_2$ of this embodiment is again designed so that the arm of the patient is kept away from the imaging area 11. The arm support device $13_2$ comprises, as above, for example a bar, ledge, rim or list having a meandering design or shape, wherein a first end thereof is fastened to the object table 4 of the arm structure 3. The arm support device $13_2$ projects a distance from the object table 4 from its fastening point of the first end, and continues in a bend, schematically indicated at reference numeral 16, in the horizontal plane before being turned upwards over the protruding part 15 and fastened at its other end to the object table 4. In this embodiment, the patient puts her arm A on the object table 4, strings her arm through the bend 16 and grabs hold of the upwards-slanting part of the arm support device $13_2$. The upper arm thus rests against the object table 4, while the forearm leans against the arm support device $13_2$. A shaded arm A is outlined in FIG. 3c in order to illustrate the use of the arm support device $13_2$.

Figure 4:
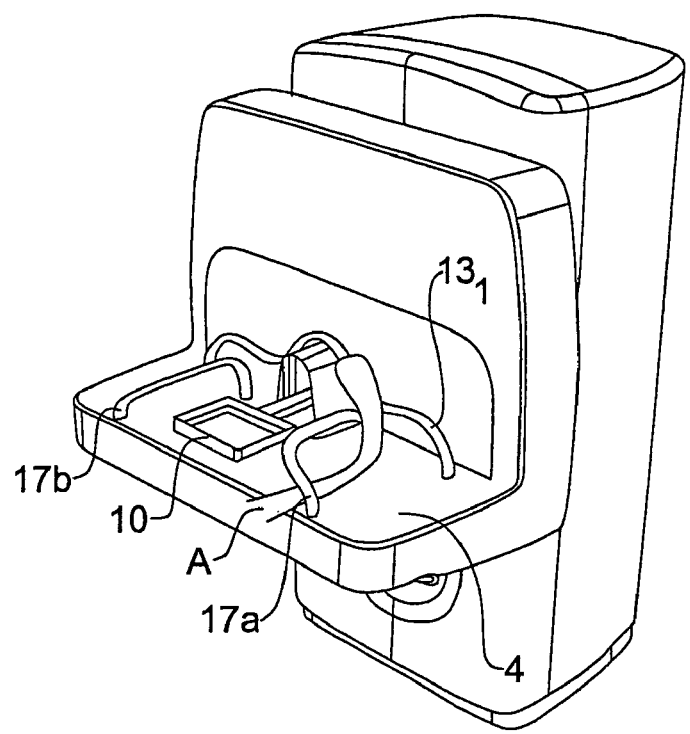
FIG. 4 illustrates yet another embodiment of the arm support device in accordance with the invention.

FIG. 4 illustrates a third embodiment of the arm support device, wherein the scanner head cover 6 is removed for clarity. The arm support device $13_1$ of the first embodiment or a similar device can be utilized and is in the third embodiment supplemented with a handle bar 17a, 17b on opposing sides of the compression plate 10 along the scanning direction (x-axis). The handle bars 17a, 17b are designed so as to provide an additional assurance of hindering the arm from being placed in the imaging area 11. In particular, the handle bar 17a is fastened at both its ends to the object table 4 and comprise a turned U-shape. The handle bar 17a is best described as having three parts: a vertical, upwards-slanting first part protruding from the object table 4, and a horizontal second part, being essentially parallel to the compression plate 10. The third part is a vertical part, preferably displaced in relation to the first part in order to enable an un-complicated insertion of the arm. More specifically, the fastening point of the first end of the handle bar 17a is displaced in relation to the fastening point of the second end as seen along the x-axis. The patient puts her arm under the first part and grabs hold of the arm support device $13_1$. A shaded arm A is outlined in FIG. 4 in order to illustrate the use of the arm support device $13_1$. The handle bar 17b is similar to the handle bar 17a, but mirror-inverted if the handle bars 17a, 17b are not symmetrical.

Figure 5:
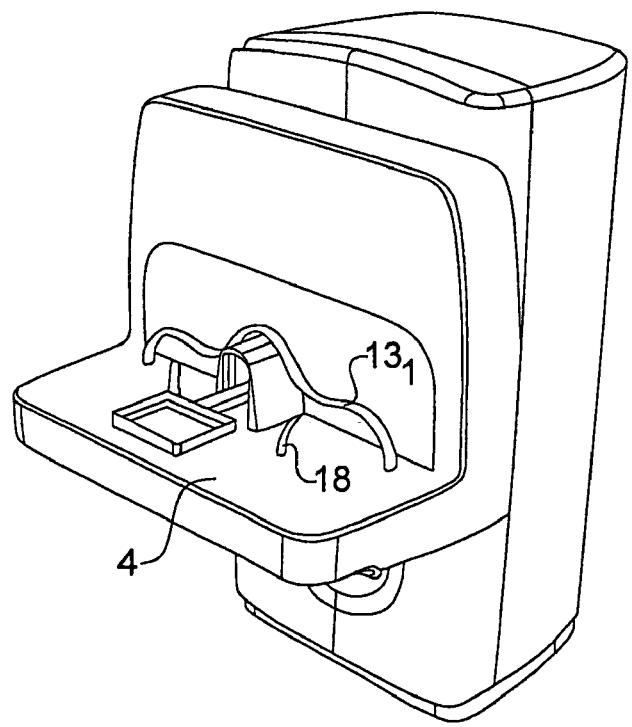
FIG. 5 illustrates still another embodiment of the arm support device in accordance with the invention.

FIG. 5 illustrates a variant of the handlebars 17a, 17b of FIGS. 4a-4c, wherein the scanner head cover 6 is removed for clarity. Instead of the handlebars 17a, 17b a set of pegs 18 are arranged to keep the elbow out of the imaging area 11. This is a more cost-efficient variant of the handlebars 17a, 17b and the pegs 18 can be swiftly attached to and detached from the object table 4.

Figure 6:
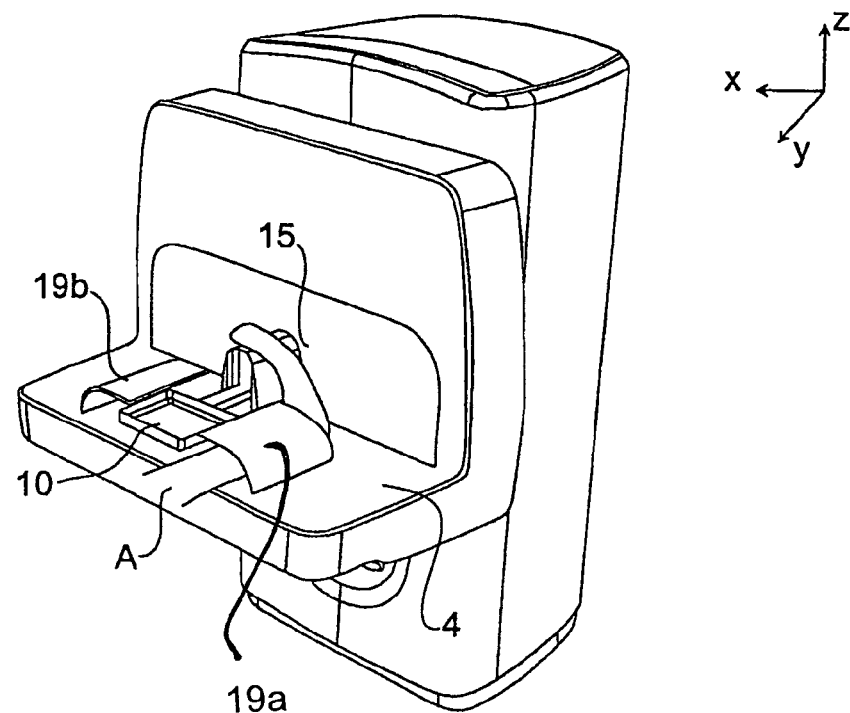
FIG. 6 illustrates still another embodiment of the arm support device in accordance with the invention.

FIG. 6 illustrates yet another embodiment of arm support device. The arm support device of this embodiment comprises two parts: the protruding part 15 of the arm structure 3 and a shield 19a. The shield 19a has a curved shape, and one edge side of it is attached to the object table 4, as illustrated in the FIG. 6. The opposing edge side is free bearing and essentially parallel to the collimator 10. The patient puts her arm under the shield 19a and rests it against the protruding part 15. There is an identical shield 19b on the other side of the compression plate 10 as seen along the x-axis for providing the same support for the other arm of the patient when imaging the other breast. The shield 19a, 19b can of course be combined with one of the earlier described arm support devices $13_1$, $13_2$. Yet again, a shaded arm A is outlined in FIG. 6 in order to illustrate the use of the arm support device 15, 19a, 19b.

Figure 7:
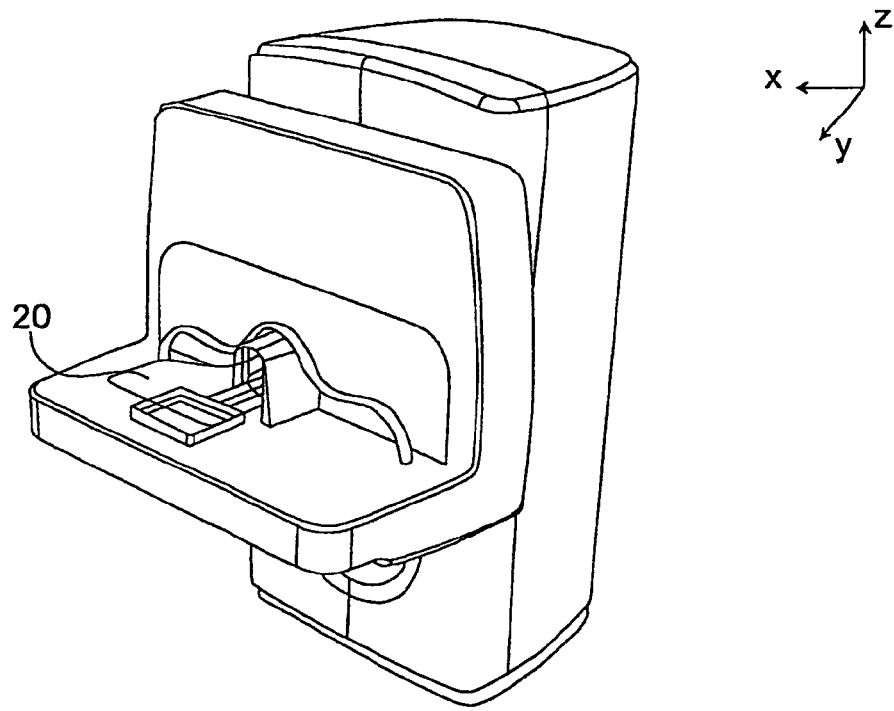
FIG. 7 illustrates a feature of the support structure in accordance with the invention.

FIG. 7 illustrates another feature of the support structure 2 for mammography in accordance with the invention. A shield 20 may be placed between the collimator 9 and the compression plate 10 for shielding the patient from the collimator 9. The shield 20 is in the example illustrated in the figure shaped as a paddle, but any shape shielding the patient from the collimator 9 is conceivable.

Figure 8A:
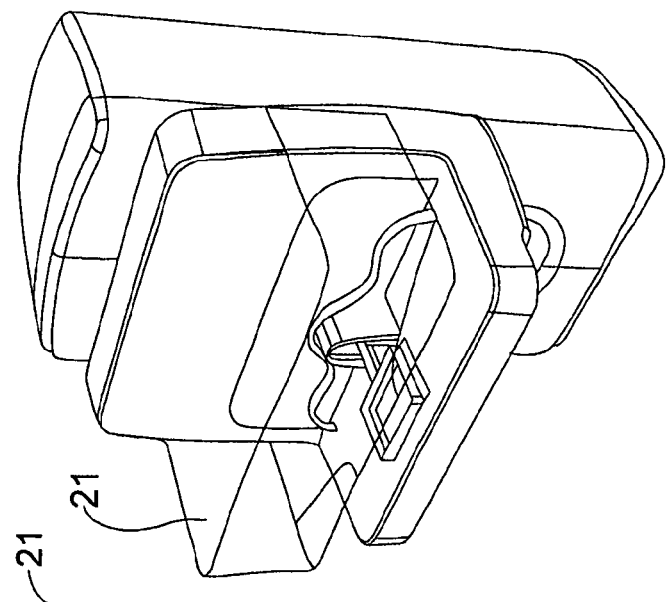
FIGS. 8*a*-8*c* illustrate a patient shield in accordance with the invention.
Figure 8B:
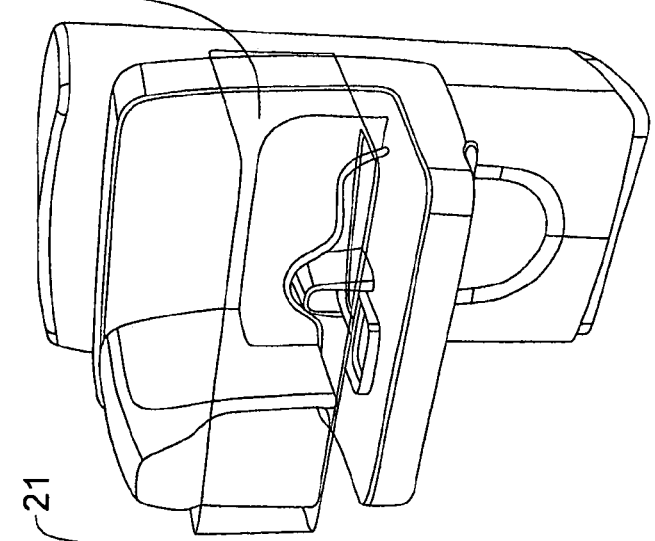
Figure 8C:
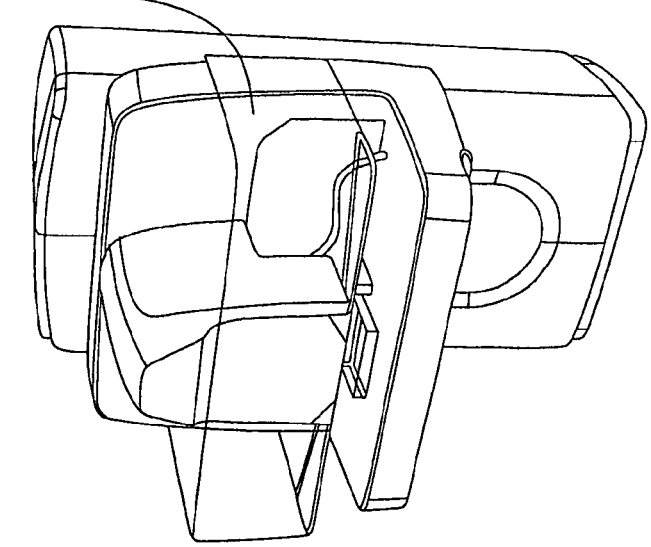

FIGS. 8a-8c illustrate still another feature of the support structure 1. A patient shield 21 is attached to the arm structure 3. The patient shield 21 has a U-shape, and can be seen as comprised of three parts: a first part extending in the y-direction, a second part extending in the x-direction and a third part parallel to the first part and thus extending in the y-direction. The patient shield 21 prevents the patient from getting in the way of the scanner head cover 6 as it moves along the x-axis during the scanning process. It is realized that the patient shield 21, although described as three parts for ease of description, is preferably made in a single piece. The patient shield 21 may further be made in a translucent material. A physician aiding the patient to put her breast in the most favourable position, can easily see through the patient shield 21 and make the positioning accordingly.

Figure 9:
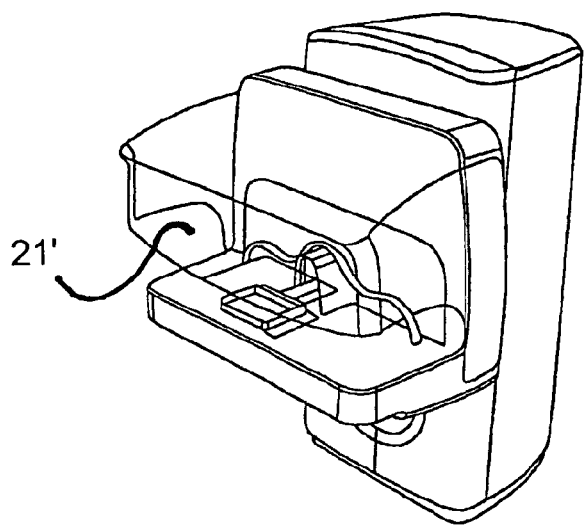
FIG. 9 illustrates another embodiment of the patient shield.

FIG. 9 illustrates a patient shield 21' having a slightly different shape. The sides of the patient shield 21' corresponding to the first and third sides of patient shield 21 described above, comprise a larger attachment surface (bond).

Figure 10:
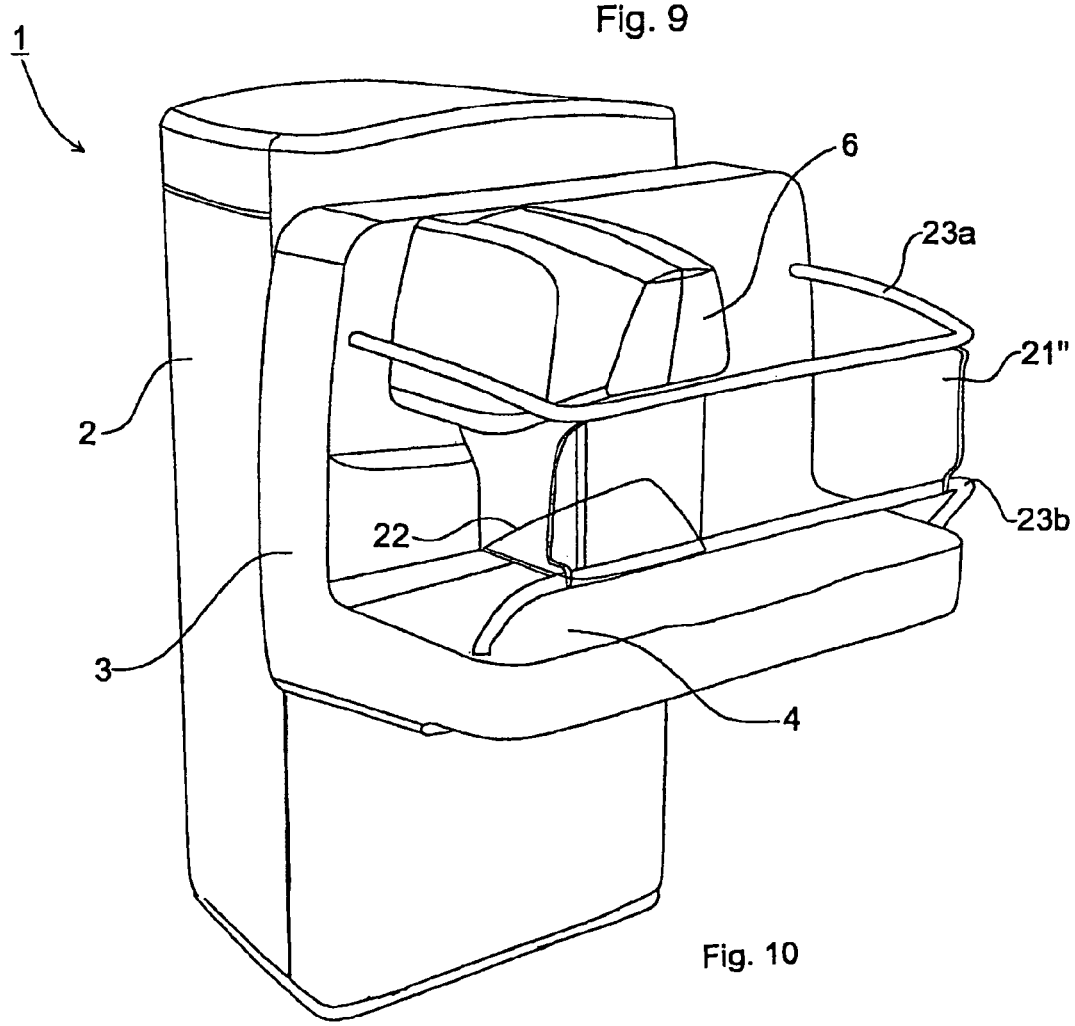
FIG. 10 illustrate yet another embodiment of the patient shield.

With reference now to FIG. 10, a third embodiment of the patient shield 21" is shown. The patient shield 21" is attached to an upper and a lower arc, 23a, 23b respectively. The upper and lower arcs 23a, 23b are attached to the arm structure 3 and have a length that allows the scanner head cover 6 to move between its two end positions.

In the figure still another feature of the invention is schematically disclosed. The scanner head cover 6 may be provided with means 22 for detecting if the patient comes in contact therewith. For example the lower side of the scanner head cover 6 being in parallel with the compression plate may be provided with touch-sensitive sensors. Such sensors can detect contact with objects, such as a body part, and send signals to a processing unit controlling the movements of the scanner head cover 6 so as to stop the scanner head cover 6. In the figure such sensor means is indicated at 22, being a strip attached to the edge of the lower side (the side parallel to the object table 4) of the scanner head cover 6. An additional security measure is thus provided.

The arm support devices $13_1$, $13_2$ described above can be made in any suitable material, for example plastics, and may for example be moulded to the desired shape.

In the above description "arm structure" is used for denoting the support structure to which the different parts are attached, for example the scanner head cover and compression plate. The "arm structure" is not to be mixed up with the description of a patient arm or arm support device. "Arm support device" is used for denoting a device for supporting the arm of a patient.

The invention claimed is:

1. A support structure for mammography, comprising:
a stand;
an arm structure attached to the stand, the arm structure including,
a substantially vertical part, and
a substantially horizontal lower part, the lower part including an X-ray detector device and an object table configured to receive a breast from a patient during imaging; and
a scanner head cover attached to the arm structure, the scanner head cover including,
an X-ray source,
a substantially vertical surface portion, and
a substantially horizontal portion, the scanner head cover defining a cavity between the vertical surface portion of the scanner head cover, the horizontal portion of the scanner head cover, and the vertical part of the arm structure, the cavity configured to receive and support a resting arm of the patient during imaging of the breast on the object table.

2. The support structure as claimed in claim 1, wherein the scanner head cover further includes a stepped shape including a recess forming a portion of the cavity.

3. The support structure as claimed in claim 1, further comprising:
an arm support device arranged on the object table so as to provide support for the arm of the patient.

4. The support structure as claimed in claim 3, wherein the object table is configured to support an upper part of the arm to rest against the object table, and wherein the arm support device is configured to support a forearm of the arm to rest against the arm support device during imaging.

5. The support structure as claimed in claim 3, wherein the arm structure further includes a protruding part arranged on the object table, the protruding part configured to hold a compression plate.

6. The support structure as claimed in claim 5, wherein the arm support device further includes a bar having a meandering shape, the bar including a first end attached to the object table, and wherein the arm support device,
projects from the object table from a fastening point of the first end of the bar,
bends in a horizontal plane,
turns upwards over the protruding part, and
fastens at another end of the arm support device to the object table.

7. The support structure as claimed in claim 6, further comprising:
a U-shaped handle bar having two ends fastened to the object table, the handle bar including,
a vertical first part protruding from the object table,
a horizontal second part, and
a vertical third part displaced in relation to the first part.

8. The support structure as claimed in claim 5, further comprising:
a shield having a curved shape, one edge side of the shield being attached to the object table, an opposing edge side of the shield being free bearing and substantially horizontal, the shield being configured to permit an upper part of the arm to lie under the shield, the protruding part being configured to support a forearm of the arm to rest against the protruding part during imaging.

9. The support structure as claimed in claim 3, wherein the arm support device further includes,
a bar having a first and a second end attached to the object table, and
a shape configured to permit at least part of the arm to rest in an upwards slanting position.

10. The support structure as claimed in claim 9, further comprising:
a handle bar arranged on the object table, the handle bar preventing the arm of the patient from being placed in an imaging area.

11. The support structure as claimed in claim 1, wherein the scanner head cover is attached to the arm structure in at least one of a rotatable and upwards and downwards movable manner.

12. The support structure as claimed in claim 1, wherein the scanner head cover is configured to scan a breast placed on an object table of the lower part of the arm structure.

13. The support structure as claimed in claim 1, wherein the arm structure is attached to the stand in a tiltable manner.

14. The support structure as claimed in claim 1, further comprising:
a patient shield attached to the arm structure so as to prevent a patient from getting in the way of the scanner head cover during a scanning process of the scanner head.

15. The support structure as claimed in claim 14, wherein the patient shield is made of a translucent material.

16. The support structure as claimed in claim 1, wherein the X-ray source is configured to move in a direction of a longest dimension of the cavity, the arm of the patient resting in the cavity in the direction of the longest dimension.

* * * * *